United States Patent [19]
Whitney et al.

[11] Patent Number: 5,489,273
[45] Date of Patent: Feb. 6, 1996

[54] INTRODUCER DEVICE AND METHODS OF USE THEREOF

[75] Inventors: James R. Whitney, Roxbury, N.H.; Michael R. Beeltje, Fitchburg, Mass.; Kenneth R. Benoit, Hinsdale, N.H.

[73] Assignee: TFX Medical, Incorporated, Jaffrey, N.H.

[21] Appl. No.: 321,206

[22] Filed: Oct. 7, 1994

[51] Int. Cl.⁶ .................................................. A61M 39/00
[52] U.S. Cl. ........................................... 604/160; 604/161
[58] Field of Search .................................. 604/160, 161, 604/165, 177

[56] References Cited

U.S. PATENT DOCUMENTS

| | | | |
|---|---|---|---|
| 3,537,451 | 11/1970 | Beck et al. | 604/165 |
| 4,834,708 | 5/1989 | Pillari | 604/165 |
| 5,141,497 | 8/1992 | Erskine | 604/160 |
| 5,167,634 | 12/1992 | Corrigan, Jr. et al. | 604/161 |
| 5,221,263 | 6/1993 | Sinko et al. | 604/161 |
| 5,380,293 | 1/1995 | Grant | 604/177 |

*Primary Examiner*—Paul J. Hirsch
*Attorney, Agent, or Firm*—David G. Conlin; Peter F. Corless

[57] ABSTRACT

An improved percutaneous introducer device is provided that inhibits or prevents undesired shearing of the splittable sheath component of the device. The device includes an interference tab that extends between two wing portions which axially shear the splittable sheath component of the device upon application of an effective force thereto. The interference tab effectively blocks undesired shearing forces that may occur during manipulation of the device by medical personnel or the patient prior to and during placement of a catheter, guide wire or other device.

18 Claims, 2 Drawing Sheets

INTRODUCER DEVICE AND METHODS OF USE THEREOF

BACKGROUND OF THE INVENTION

1. Field of the Invention

The present invention relates to an introducer device for insertion of a catheter, guide wire and the like into a patient and, more particularly, an improved introducer device comprising a splittable sheath component.

2. Background

Splittable introducer devices have been employed for inserting catheters, guide wires and the like into patients. A typical procedure provides for insertion of a hollow needle encased within a splittable sheath into a vein of a patient. After insertion, the needle may be removed leaving the sheath protruding from the patient's vein. A catheter such as a central venous access catheter or guide wire is then threaded through the sheath into the patient. The encasing sheath is then longitudinally sheared and removed from the catheter or guide wire and the patient such as by applying opposing force to opposed wings or tabs of the introducer device. See U.S. Pat. Nos. 5,334,157; 5,221,263; 5,141,497; and 5,098,392.

As should be apparent, such an introducer device can be subjected to significant manipulation prior to the intended shearing and removal of the sheath component once a catheter or the like has been positioned within a patient. It is generally necessary or at least desirable, however, that the sheath component not split earlier than intended. Such premature splitting can prevent or at least make more difficult insertion and placement of a catheter or guide wire.

One attempt to address this problem has been reported in U.S. Pat. No. 5,334,157. However, that patent describes a device that includes a type of locking mechanism between a needle hub and sheath component. Such a locking mechanism can be inconvenient as additional engaging and disengaging steps for the locking mechanism are required. Additionally, the locking mechanism can add to production time and costs.

SUMMARY OF THE INVENTION

The present invention comprises an improved percutaneous introducer device that inhibits or prevents undesired shearing of the splittable sheath component of the device. The device includes an interference tab that extends between two wing portions which axially shear the splittable sheath component of the device upon application of an effective force thereto. The interference tab effectively blocks undesired shearing forces that may occur during manipulation of the device by medical personnel or the patient prior to and during placement of a catheter, guide wire or other device. Moreover, the interference tab is not rigidly attached to either the splittable sheath or the wing portions of the device. This configuration provides significant advantages, including obviating any need to engage or disengage the interference tab such as would be required with a locking-type system.

More particularly, the invention provides an introducer device that includes a 1) splittable sheath component comprising a bore adapted to receive a percutaneous needle for insertion into a vein of a patient while circumscribed by the sheath; 2) two opposed wing portions attached to the splittable sheath, the wing portions capable of splitting the sheath upon application of an effective shearing force to the wing portions; 3) a needle for insertion into a vein of a patient while circumscribed by the sheath; 4) a hub portion attached to the proximal end of the needle, the hub portion comprising an interference tab that extends from the hub portion, and positioned between the wing portions without attachment to the splittable sheath when the needle is inserted through the sheath, and whereby the interference tab inhibits splitting of the sheath due to force applied to one or more of the wing portions. Preferably the wing portions of the device are disposed at an acute angle with respect to one another, and together form an outwardly open slot that extends axially along the plane of device from which the wing portions protrude, and the interference tab longitudinally extends through that slot. In particularly preferred aspects of the invention, the interference tab extends through the substantial length of the slot. Typically the interference tab is substantially rectangular or cylindrically shaped, although other configurations may be employed provided the tab effectively inhibits premature splitting of the sheath component that may arise from force applied to one or more of the wing portions.

In a preferred aspect of the invention, an introducer device is provided that includes a splittable sheath component comprising a bore adapted to receive a hollow needle for insertion into a vein of a patient while circumscribed by the sheath, and two opposed wing portions attached thereto, the wing portions capable of splitting the catheter upon application of an effective shearing force to the wing portions, and wherein the top proximal ends of the wing portions together form a lead-in section that aids insertion of a catheter or the like into the splittable sheath.

It is further preferred that the wing portions do not completely circumscribe the sheath component, but rather the wing portions are non-integral components that are separated, preferably on each of opposing sides, by the underlying splittable sheath. By this configuration, the wing portions are not split during shearing of the sheath, i.e. the sheath can be sheared along the surface interposed between the separated wing portions, thereby facilitating the shearing process.

Methods of the invention include means for inserting a catheter or guide wire into a selected vein of a patient that comprises piercing a selected vein of a patient with an introducer device of the invention; withdrawing the needle of the introducer device from the splittable sheath component and inserting a catheter or guide wire through the splittable sheath component into the selected vein; and applying inwardly cooperating forces to the wing portions to thereby axially shear the sheath.

These and other features and objects of the invention will be readily understood from the following detailed description of the invention which should be read in light of the accompanying drawings.

DETAILED DESCRIPTION OF THE INVENTION

Figure 1:
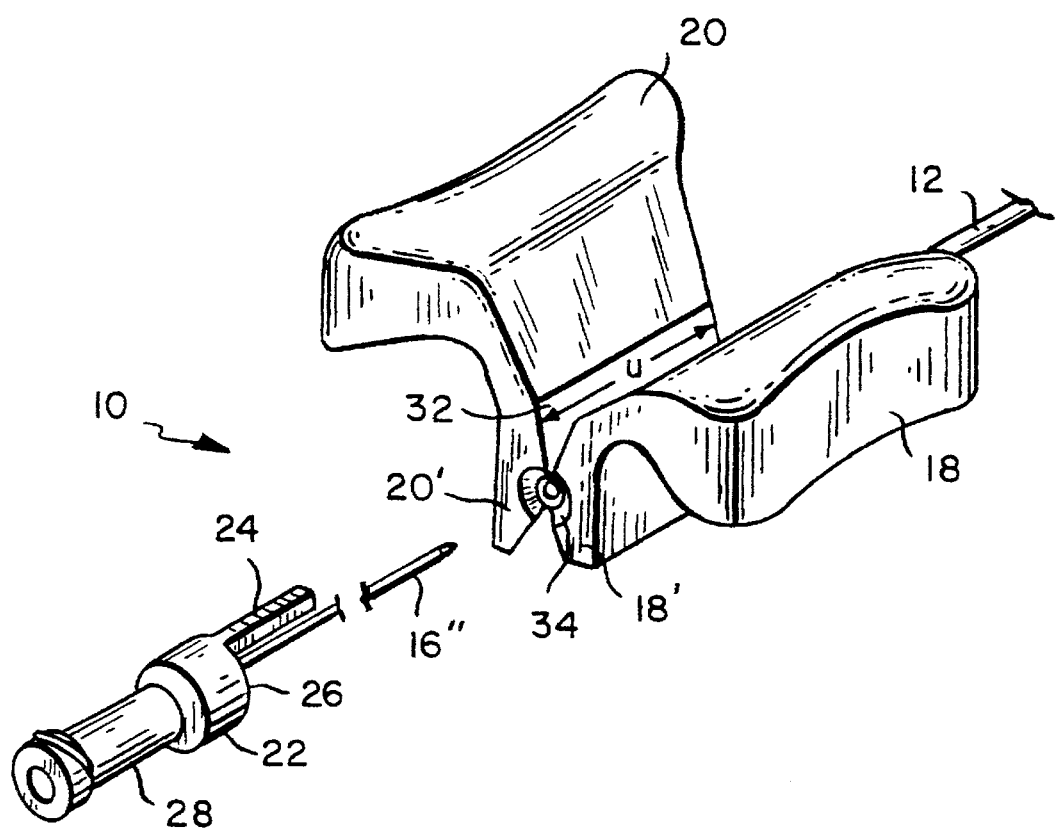
FIG. 1 shows an above view of separated splittable sheath and needle components of an introducer device of the invention.
Figure 2:
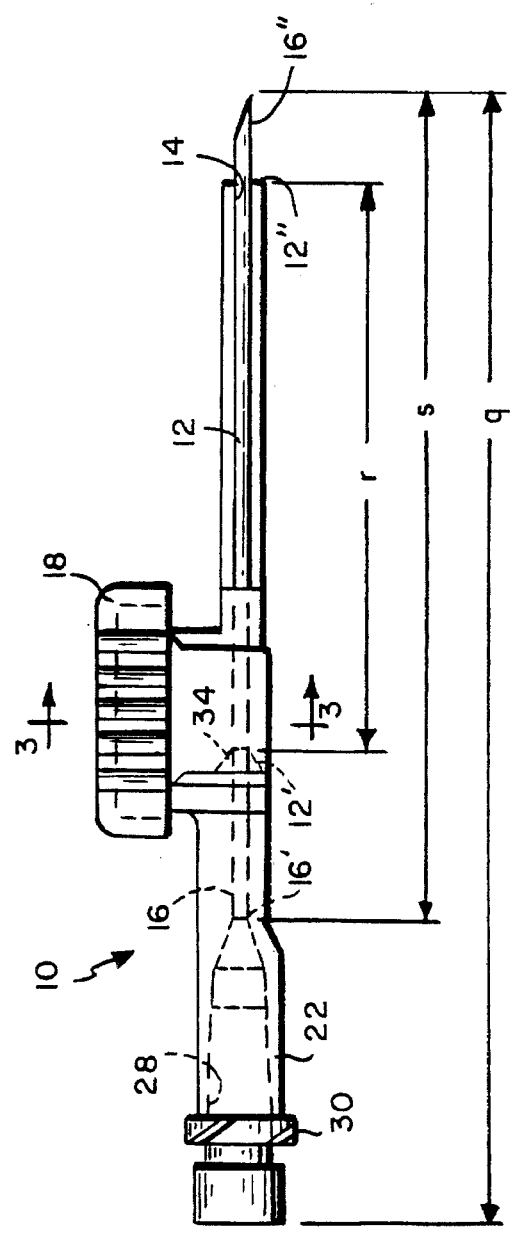
FIG. 2 shows a cut-away side view of an introducer device of the invention wherein the needle component is circumscribed by the splittable sheath component.

Referring now to the Drawings, where particularly preferred introducer devices of the invention are depicted, FIGS. 1–2 shows introducer device 10 that includes splittable sheath component 12 having a bore 14 adapted to receive hollow needle 16 that is inserted into a selected vein of a patient. Two opposed wing or tab portions 18 and 20 are attached to splittable sheath 12. Preferably wing portions 18 and 20 protrude from the device at an acute angle with respect to each other as depicted in FIG. 1.

Figure 3:
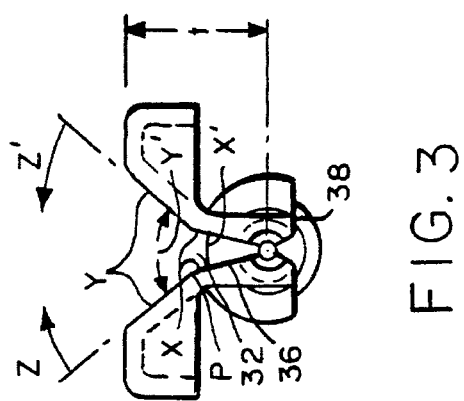
FIG. 3 shows a cross-sectional view taken along the line 3—3 of FIG. 2.

Preferably each wing portion has a substantially "inverted L" shape as clearly shown in FIGS. 1 and 3, where facing opposed surfaces of each wing portion open to a wider angle along their length, preferably at a point (shown as p in FIG. 3) positioned about one-quarter to one-half upward along the length of the opposing surfaces, more preferably about one-third along the length of the opposing wing portion surfaces as is clearly depicted in FIG. 3. Thus, as shown in FIG. 3, the opposed surfaces x proximate to sheath 12 of each of wing portions 18 and 20 are positioned at a narrower angle with respect to each other relative to the angle the more distal contiguous opposed surfaces y are positioned with respect to each other. That is, angle x' formed by respective surfaces x of portions 18 and 20 is less than angle y' formed by respective surfaces y of portions 18 and 20, as shown e.g. in FIG. 3.

This configuration provides significant advantages including a "two-click" or "two-cam" action upon engaging wing portions 18 and 20 by applying inward pressure thereto in the directions Z and Z' as shown in FIG. 3. That is, upon engaging the wing portions, first the opposing x surfaces of portions 18 and 20 are mated. That first "click" can serve to position the underlying sheath properly for splitting. Additional force applied in directions Z and Z' then bring opposing surfaces y and y' further toward one another (the second "click") which effects the axial shearing of the underlying sheath. While the angles x' and y' can be a variety of values, preferably x' is between about 20 and 45 degrees and y' is between about 30 and 90 degrees.

While such an inverted L shape is preferred, wing portions of other shapes could be employed. For example, the wing portions each could be substantially flat (together substantially V-shaped) or outwardly rounded, provided the wing portions could be engaged to effect shearing of the sheath component as desired.

Figure 4:
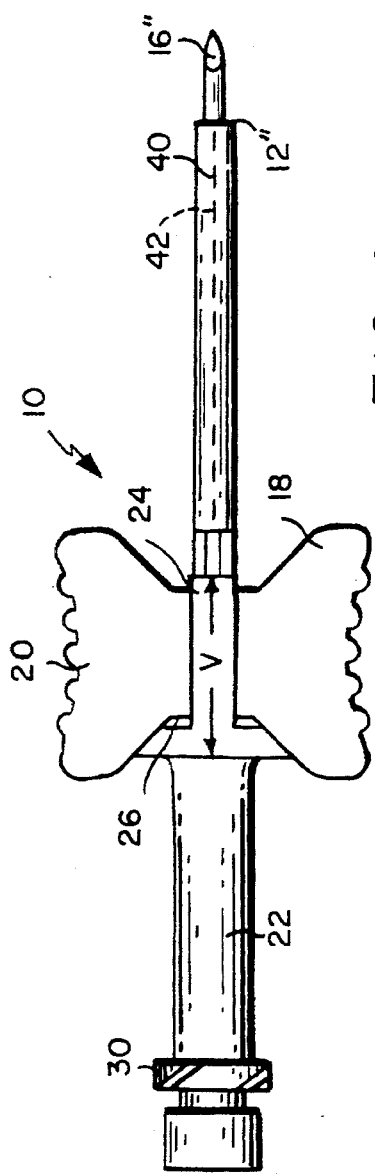
FIG. 4 shows an above view of an introducer device of the invention wherein the needle component is circumscribed by the splittable sheath component.

It is also preferred that the outer surface of wing portions 18 and 20 include topography to aid handling and manipulation of the introducer device. In particular, and as shown in FIGS. 2 and 4, preferably the exposed sides of wing portions 18 and 20 are ridged or have other topography to facilitate handling and manipulation of device 10.

A hub portion 22 is attached to the proximal end 16' of hollow needle 16. As used herein, unless otherwise indicated, the term proximal is intended to designate the specified end closest to the medical personnel manipulating the introducer device, and the term distal is intended to designate the specified end closest to the patient. As clearly shown in FIG. 1, hub portion 22 includes interference tab 24 that extends from bottom face 26 of hub 22. Preferably the hub portion also includes an upwardly extending, open-ended flash chamber 28 that receives blood flowing upward through bored needle 16 when sharpened distal end 16" pierces a patient's vein, thereby informing the medical personnel the needle has been successfully inserted. As can be clearly seen in FIG. 2, the distal end of hub portion 22 includes a narrow bore that is adapted to firmly engage needle 16. At the needle proximal end 16', the bore within hub 22 expands to form flash chamber 28 as can be clearly seen in FIG. 2.

Preferably the distal portion of hub 22, on the side opposite that from which wing portions 18, 20 outwardly extend, tapers inward to provide an inset or flatter profile on that plane of the device such as is depicted in FIG. 2. This configuration enables the device to be more securely and conveniently placed on a patient (e.g. on the patient's forearm), and also facilitates access to and manipulation of proximal ends of needle 16 and hub 22 by medical personnel. It is particularly preferred that the hub portion taper commences at a position proximate to needle proximal end 16' as shown in FIG. 2. It is also preferred that the "back side" of wing portions 18 and 20 do not extend significantly below the plane of the tapered hub as is shown in FIG. 2, i.e. the tapered hub and wing portions form a substantially or essentially contiguous or even plane on the side of the device opposite that from which the outwardly extended wing portions are engaged.

Preferably a top lip 30 with luer threads is formed on the outer surface of the proximal end of hub portion 22 and is adapted to receive a syringe for administration to a patient via needle 16. Also preferred is where flash chamber 28 includes a luer taper within hub 22 as depicted in FIG. 2 to receive a syringe for administration to a patient via needle 16.

As clearly shown in FIGS. 1 and 3, wing portions 18 and 20 preferably together form therebetween an outwardly open slot 32 that is adapted to receive interference tab 24 when needle 16 is inserted through splittable sheath 12. For use of device 10, needle 16 is fully inserted into sheath 12 so that hub bottom face 26 mates and rests on the top proximal ends 18' and 20' of wing portions 18 and 20, and sharpened needle distal end 16" protrudes from splittable sheath distal end 12" and can be inserted into a selected vein of a patient. As can be seen e.g. in FIG. 4, interference tab 24 is nested within axially extending slot 32 without attachment to sheath 12 or wing portions 18, 20 whether by a latching mechanism or any other locking-type attachment means. As discussed above, this system obviates the need for any inconvenient engaging or disengaging step that would be required if a locking-type mechanism or other positive attachment means was employed. It should be appreciated that slot 32 can be a variety of configurations, e.g. U-shaped, V-shaped or substantially rectangular, provided that interference tab 24 can be effectively nested therein.

In such nested position as shown in FIG. 4, interference tab 24 will prevent or inhibit undesired shearing of splittable sheath 12 that may occur as forces are inadvertently applied to wings 18, 20 during manipulation of device 10 during insertion and withdrawal of needle 16 and insertion and placement of a catheter, guide wire or the like.

In a preferred aspect of the invention, wing portion top proximal ends 18' and 20' together form a lead-in section 34, preferably tapered or substantially conically shaped as shown in FIGS. 1–3, and which aids insertion of a catheter, guide wire or the like into the splittable sheath. Preferably wing portion proximal ends 18' and 20' each comprise an inwardly sloping, semi-circular portion of the lead-in section whereby the mated wing portions form lead-in section 34. As can be seen in FIG. 2, sheath proximal end 12' mates with lead-in section 34.

It is preferred that wing portions 18 and 20 are non-integral components, i.e. wings 18 and 20 are unattached components, preferably separated on each of opposing sides by the underlying splittable catheter portions 36 and 38 as can be seen in FIG. 3. As discussed above, by this configuration, the wing portions are not split during shearing of the sheath, thereby facilitating the shearing process. Nevertheless, if desired, wing portions 18 and 20 could be attached and thereby circumscribe portions 36 and/or 38 as well as the rest of the periphery of the splittable sheath. For such a design, the wing portions should include suitable means for shearing of the attached wing portions upon shearing of the sheath component, e.g. the attached wing portions could include a scored or otherwise weakened surface(s) axially aligned with intended lines of shearing of the sheath.

Wing portions 18 and 20 and splittable sheath 12 are preferably formed in an insert molding process as is known in the art wherein the sheath 12 is extruded and then the wing portions are molded directly thereon. It also would be possible to separately form the wing portions and then adhere those portions onto the separately formed sheath such as by a suitable adhesive. Although generally less desired, it is also possible to interpose a hub or mounting unit between wing portions 18 and 20 and the splittable catheter 12. For example, plastic strips can be first affixed to catheter 12 and then wing portions 18 and 20 mounted on and affixed to such plastic strips. Preferably sheath 12 and wing portions 18 and 20 are formed from a polyethylene, although clearly other materials could be used as will be appreciated by those skilled in the art. For example, sheath 12 could be formed from a tetrafluoroethylene polymer (TEFLON).

Preferably splittable sheath 12 includes axially extending, diametrically opposed score lines 40 and 42 to facilitate axial shearing upon engaging wing portions 18 and 20. Score lines 40 and 42 should each traverse interposed portions 36 and 38.

Sharpened, hollow needle 16 is suitably fabricated from stainless steel as is known in the art. The hub portion 22 is suitably rigid plastic such as a polyethylene, preferably with extended chamber 28 being substantially transparent so blood received therein can be readily observed. Interference tab 24 will typically be an integral component of hub 22 such as may be formed by an injection molding process or, alternatively, tab 24 may be separately formed from plastic or metal, preferably plastic, and then attached to hub bottom face 26 such as by an adhesive.

Suitable dimensions of the components of an introducer device of the invention can suitably vary rather widely and can be readily determined by those skilled in the art based on the present disclosure. In general, splittable sheath 12 and needle 16 should have a diameter capable of being inserted within a selected vein of a patient, and sheath 12 should have a diameter sufficient to accommodate a catheter, guide wire or the like. Preferably the diameter of splittable sheath 12 is between about 0.76 mm and 2.26 mm; and the diameter of needle 16 is between about 0.71 mm and 2.13 mm. Preferably the overall length of introducer device 10, represented as length q in FIG. 2, is between about 76.2 mm and 79.4 mm, with the length of splittable sheath 12 (represented as distance r in FIG. 2) being between about 41.9 mm cm and 42.7 mm, and the length of needle 16 (represented as distance s in FIG. 2) being between about 58.4 mm and 59.2 mm. Wing portions 18 and 20 preferably have a relatively flat profile and the distance t shown in FIG. 3, extending from a centerpoint of splittable sheath 12 to the top side face of the wing portions, is preferably between about 9.60 mm and 10.11 mm. Preferably the length of slot 32 (distance u in FIG. 1) is between about 8.64 mm and 9.14 mm. As discussed above, preferably interference tab 24 extends downward through at least a substantial portion of the length of slot 32, e.g. about 50, 70 or 80 percent or more of the length of the slot. More preferably interference tab 24 extends the entire length of slot 32 as depicted in FIG. 4. For preferred lengths of slot 34 as disclosed above, preferably the length of interference tab 24, as shown by length v in FIG. 4, is between about 11.18 mm and 11.68 mm.

A particularly preferred introducer device of the invention is of the configuration shown in the Drawings, wherein the overall length of introducer device 10 (length q) is 77.8 mm; the length of splittable sheath 12 (length r) is 42.3 mm and the splittable sheath is formed from polyethylene having a wall thickness of 0.165 mm; the length of needle 16 (length s) is 58.8 mm; wing portions 18 and 20 protrude (distance t) 9.85 mm; and the length of slot 28 (length u) is 8.89 mm and the interference tab 24 extends the entire length of slot 32 as depicted in FIG. 4.

An introducer device of the invention may be suitably used as follows for placement of a catheter, guide wire or the like in a patient. The introducer device 10 is inserted into a selected patient by means of sharpened distal needle end 16" as may be verified by blood flashback observed in chamber 28. Needle 16 with attached hub 22 is then withdrawn from the splittable sheath 12 which remains in the vein of the patient. A catheter or the like is then threaded through the splittable sheath component (as may be assisted by lead-in section 34) and then into the vein. After desired placement of the catheter, the sheath is sheared by substantially opposite inward force applied by the fingers of a single hand in the directions Z and Z' depicted in FIG. 3. That inward force operates to shear the sheath along the score lines thereof as discussed above.

The foregoing description of the present invention is merely illustrative thereof, and it is understood that variations and modification can be made without departing from the spirit or scope of the invention as set forth in the following claims.

What is claimed is:

1. An introducer device comprising:
   (a) a splittable sheath having a bore adapted to receive a needle for insertion into a vein of a patient while circumscribed by the sheath;
   (b) two opposed wing portions attached to the sheath, the wing portions capable of splitting the sheath upon application of an effective shearing force to the wing portions;
   (c) a needle for insertion into a vein of a patient while circumscribed by the sheath;
   (d) a hub portion attached to the proximal end of the needle, the hub portion comprising an interference tab that extends from the hub portion, and is positioned between the wing portion and without positive attachment to the wing portions or the sheath when the needle is inserted through the sheath, and whereby the interference tab inhibits splitting of the sheath due to force applied to one or more of the wing portions.

2. The introducer device of claim 1 wherein the wing portions extend from the device at an acute angle with respect to each other.

3. The introducer device of claim 2 wherein facing opposed surfaces of each wing portion open to a wider angle along the length of the wing portions.

4. The introducer device of claim 1 wherein the distal portion of the hub tapers inward on the side of the device opposite that from which the wing portions outwardly extend and are engaged.

5. The introducer device of claim 1 wherein the wing portions form therebetween an outwardly open slot that longitudinally extends along the plane of device from which the wing portions protrude, and the interference tab longitudinally extends through the slot.

6. The introducer device of claim 5 wherein the interference tab extends at least substantially through the length of the slot.

7. The introducer device of claim 1 wherein the interference tab is substantially rectangular or cylindrically shaped.

8. The introducer device of claim 1 wherein the top ends of the wing portions together form a lead-in section that aids insertion of a catheter or guide wire through the splittable sheath.

9. The introducer device of claim 1 wherein each of the wing portions are affixed to opposing sides of the splittable sheath.

10. The introducer device of claim 1 wherein the splittable sheath is not completely circumscribed by the two wing portions.

11. The introducer device of claim 10 wherein the wing portions are not sheared upon shearing of the splittable sheath.

12. The introducer device of claim 1 wherein the splittable sheath has opposed longitudinally extending score lines which assist shearing of the splittable sheath upon application of effective force to the wing portions.

13. The introducer device of claim 1 wherein the hub extends above the proximal end of the needle and forms a chamber for receiving blood flowing through the needle after vein penetration by the needle distal end.

14. The introducer device of claim 1 wherein device does not contain a locking-type mechanism for attachment of interference tab to the sheath or wing portions.

15. The introducer device of claim 10 wherein the two wing portions are unattached with respect to each other and are separated on opposing sides by the underlying splittable catheter.

16. An introducer device comprising:
(a) a splittable sheath having a bore adapted to receive a needle for insertion into a vein of a patient while circumscribed by the sheath;
(b) two opposed wing portions attached to the sheath, the wing portions capable of splitting the sheath upon application of an effective shearing force to the wing portions, the top ends of each of the wing portions together only partially circumscribing the sheath and forming a lead-in section that aids insertion of a catheter or guide wire through the splittable sheath, and the two wing portions are unattached with respect to each other;
(c) a needle for insertion into a vein of a patient while circumscribed by the sheath;
(d) a hub portion attached to the proximal end of the needle, the hub portion comprising an interference tab that extends from the hub portion, and whereby the interference tab inhibits splitting of the sheath due to force applied to one or more of the wing portions.

17. The introducer device of claim 16 wherein the two wing portions are separated on opposing sides by the underlying splittable catheter.

18. A method of introducing a catheter or guide wire into a patient comprising:
(a) providing an introducer device comprising
(i) a splittable sheath having a bore adapted to receive a needle for insertion into a vein of a patient while circumscribed by the sheath;
(ii) two opposed wing portions attached to the sheath, the wing portions capable of splitting the sheath upon application of an effective shearing force to the wing portions;
(iii) a needle for insertion into a vein of a patient while circumscribed by the sheath;
(iv) a hub portion attached to the proximal end of the needle, the hub portion comprising an interference tab that extends from the hub portion, and is positioned between the wing portion and without positive attachment to the wing portions or the sheath when the needle is inserted through the sheath, and whereby the interference tab inhibits splitting of the sheath due to force applied to one or more of the wing portions;
(b) inserting the distal end of the introducer device into a selected vein of a patient;
(c) withdrawing the needle from the sheath and inserting a catheter or guide wire through the sheath into the selected vein; and
(d) applying inwardly cooperating forces to the wing portions to axially shear the sheath.

* * * * *